US006231549B1

(12) United States Patent
Noecker et al.

(10) Patent No.: US 6,231,549 B1
(45) Date of Patent: May 15, 2001

(54) SHIM DEVICE FOR ENTERAL FEEDING SYSTEM

(75) Inventors: Angela M. Noecker, Richmond Heights; Kevin C. Meier, St. Louis, both of MO (US)

(73) Assignee: Sherwood Services, AG (CH)

( * ) Notice: Subject to any disclaimer, the term of this patent is extended or adjusted under 35 U.S.C. 154(b) by 0 days.

(21) Appl. No.: 09/375,925

(22) Filed: Aug. 17, 1999

(51) Int. Cl.[7] ...................................................... A61M 5/32

(52) U.S. Cl. .......................... 604/175; 604/174; 604/513; 604/164.04; 128/DIG. 26; 606/108

(58) Field of Search .................................... 604/174, 175, 604/177, 178, 116, 117, 250, 506, 513, 103.03, 164.04; 128/DIG. 26; 606/108

(56) References Cited

U.S. PATENT DOCUMENTS 5,248,302 9/1993 Patrick et al. .
5,620,419 * 4/1997 Lui et al. ............................. 604/116
5,902,275 * 5/1999 Dobkin ................................. 604/174
5,916,200 * 6/1999 Eppley et al. ....................... 604/178

* cited by examiner

*Primary Examiner*—Richard K. Seidel
*Assistant Examiner*—Jennifer Maynard
(74) *Attorney, Agent, or Firm*—Greensfelder, Hemker & Gale, P.C.

(57) ABSTRACT

A shim device is provided for use with a low profile gastrostomy device having a gastrostomy tube fitted in a mature stoma and held in place between an internal retention mechanism disposed within a visceral organ of a patient and an external retention mechanism seated on the outer abdominal wall of a patient. Further, the shim device provides an adjustable shim body which is inserted between the external retention mechanism and the patient for accommodating the gradual growth of the patient during convalescence. The shim device also operates to evenly distribute the weight of the low profile gastrostomy device over a patient's outer body.

13 Claims, 3 Drawing Sheets

SHIM DEVICE FOR ENTERAL FEEDING SYSTEM

BACKGROUND OF THE INVENTION

1. Field of the Invention

The present invention relates to a medical device for use with enteral feeding systems, and more particularly to a support arrangement for use with a low profile gastrostomy tube inserted inside a patient. More specifically, the present invention relates to an adjustable shim device for accommodating the gradual growth of a patient during convalescence.

2. Prior Art

Enteral feeding systems are frequently used for long term tube fed patients who require some type of gastrostomy device to provide nutrition to a patient unable to take nutrition orally. These enteral systems typically comprise an administration tubing set attached to a source of nutrition at one end and some kind of enteral feeding tube at the other end for providing nutrition directly to a patient's stomach or small intestine. A standard gastrostomy tube properly inserted inside a viscera of a patient usually extends outwardly a distance from the patient's outer abdominal wall which the patient may find inconvenient or uncomfortable due to the high profile of the gastrostomy tube relative to the patient. Further, the outwardly extending gastrostomy tube may present an unsightly appearance to some patients. Accordingly, a low profile gastrostomy tube was developed to provide a less intrusive alternative to the standard gastrostomy tube arrangement.

The low profile gastrostomy tube is normally inserted into and through a stoma formed in the patient's abdominal wall utilizing an internal retention member disposed inside a patient's viscera to anchor the free end of the gastrostomy tube therein, while an external retention member is seated on the patient's outer abdominal wall with a tubular member attached between the respective retention members. The tubular member provides a fluid pathway between the administration tubing set connected to a source of nutrition and the internal retention member of the low profile gastrostomy tube disposed inside the patient. The internal retention member attaches to a distal or free end of the low profile gastrostomy tube to hold and affix a hollow organ of choice, e.g. the stomach, against the posterior abdominal wall of a patient. The hollow organ is affixed by capturing the organ wall and the abdominal wall between the external retention member seated on the outer abdominal wall of a patient and the internal retention member anchored inside the patient's viscera.

A typical internal retention member is disclosed in U.S. Pat. No. 5,248,302 to Patrick et al. entitled "Percutaneous Obturatable Internal Anchoring Device" which describes a deformable obturatable internal retention member designed to pass through a stoma formed in a wall of the abdomen and stomach or other viscera of a patient in order to secure the low profile gastrostomy tube within the organ of choice and is herein incorporated by reference in its entirety. The method of using this type of obturatable internal retention member consists of inserting an obturator rod through the tubular member of the low profile gastrostomy tube until the rod abuts or engages the distal end of the internal retention member. The internal retention member comprises a plurality of flexible retaining arms attached to the hollow tubular member that mechanically elongate and thereby slenderize the silicone or polyurethane retaining arms to a size about that of the diameter or the tubular member when the obturator rod is pushed axially toward the patient. Such slenderization of the retaining arms allows safe insertion or removal of the tubular member and internal retention member into or from an established, matured stoma of a patient. Such obturatable internal retention members are one of many current means used to insert, anchor and secure the low profile gastrostomy tube in a matured stoma of a patient.

After the internal retention member has been inserted inside the stomach, the obturator rod is withdrawn through the tubular member which allows the flexible retaining arms of the internal retention member to assume their preset enlarged shape, thereby retaining the internal retention member inside the stomach so that it cannot be withdrawn back through the stoma. Once the internal retention member assumes its preset enlarged shape the feeding tube with a connection member at one end is attached to the external retention member of the low profile gastrostomy tube in order to establish fluid flow communication between the source of nutrition and the patient's stomach. In this way, nutrition is provided directly to the patient's stomach through the low profile gastrostomy tube. Unfortunately, the current low profile gastrostomy tube arrangement may often require an extra space between the patient's outer skin and the external retention member in order to later accommodate the patient's growth as he or she adds weight during convalescence, thereby gradually filling up the extra space. Further, the external retention member is required to be seated on the patient's stomach for long periods of time while the patient is being fed through the low profile gastrostomy tube. This long term, continuous contact between the legs of the external retention member and the patient's outer abdominal wall can cause pressure necrosis of the patient's skin.

Therefore, there appears to be a need in the art for a shim device that is adjustable and can accommodate the gradual growth of a patient as he or she adds weight without changing shim devices. Further, there is a need in the art for a shim device that supports the weight of an external retention member of a low profile gastrostomy tube in order to more evenly distribute the weight of the external retention member over a wider area of the patient's outer abdominal wall, while also taking up any extra space between the external retention member and the patient's skin.

OBJECTS AND SUMMARY OF THE INVENTION

In brief summary, the present invention overcomes and substantially alleviates the deficiencies in the prior art by providing an adjustable shim device for accommodating the gradual growth of a patient during convalescence. The shim device of the present invention comprises a shim body having a top side and a bottom side with a plurality of pads extending perpendicularly from each side of the shim body. The plurality of pads are adapted to support and evenly distribute the weight of an external retention member of a low profile gastrostomy tube over an area of a patient's outer skin layer. The plurality of pads formed on one side of the shim body are of a greater height than the pads formed on the opposing side, so that pads on one side will support the external retention member at a greater distance from the patient's body than the pads located on the opposing side. This differential in pad height between the two opposing sides of the shim body provides for an adjustable shim device of the present invention with two alternative heights for supporting the external retention member depending on which side of the shim body is placed on the patient's outer skin layer.

The shim body of the present invention further includes a center portion which defines an axial opening and four outer portions that extend outwardly from the inner portion which, in conjunction with the pads, provide the means for supporting and evenly distributing the weight of the external retention member on the patient. Two small pads are provided along the outer edge of each outer portion for evenly distributing the weight of the external retention member along the outer portions of the shim body, while four large pads are positioned around the inner portion for evenly distributing that same weight around the inner portion of the shim device. In the preferred arrangement, one large pad is juxtapositioned between each respective outer portion along the inner portion. A pair of apertures are formed between any two inner pads for providing air circulation between the space formed between the pads when the shim device is seated on the patient. Finally, a radial slit is formed along one of the four outer portions between the outer edge of the particular outer portion and the axial opening which allows the user to spread apart the outer portion in order to slide the axial opening around a tubular member when attaching the shim device to the low profile gastrostomy tube.

Accordingly, the primary object of the present invention is to provide an adjustable shim device having a dual height feature which permits alternatively supporting a portion of a gastrointestinal enteral feeding system at two different heights depending on which side of the shim device is placed on the patient's body;

Another object of the present invention is to provide a shim device for supporting and evenly distributing the weight of at least a portion of a gastrointestinal feeding system on a patient's body;

A further object of the present invention is to provide a shim device for filling in the extra space between the external retention member and the patient's body; and Another further object of the present invention is to provide a shim device made of a flexible, resilient material.

These and other objects of the present invention are realized in the preferred embodiment of the present invention, described by way of example and not by way of limitation, which provides for a shim device for supporting and evenly distributing the weight of a gastrointestinal feeding system on a patient's body.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1A:
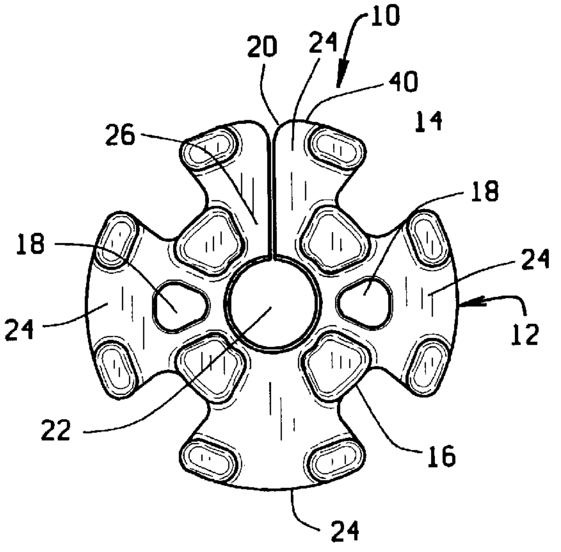
FIG. 1*a* is planar top view of the shim device according to the present invention.
Figure 1B:
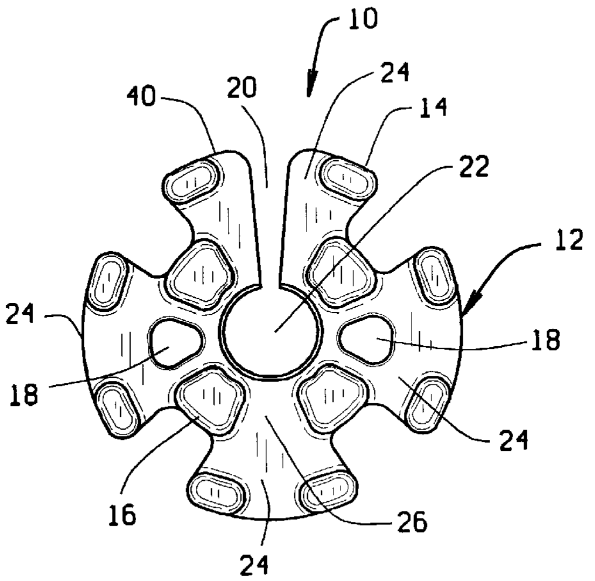
FIG. 1*b* is a planar bottom view of the shim device showing the slit spread apart according to the present invention.
Figure 4:
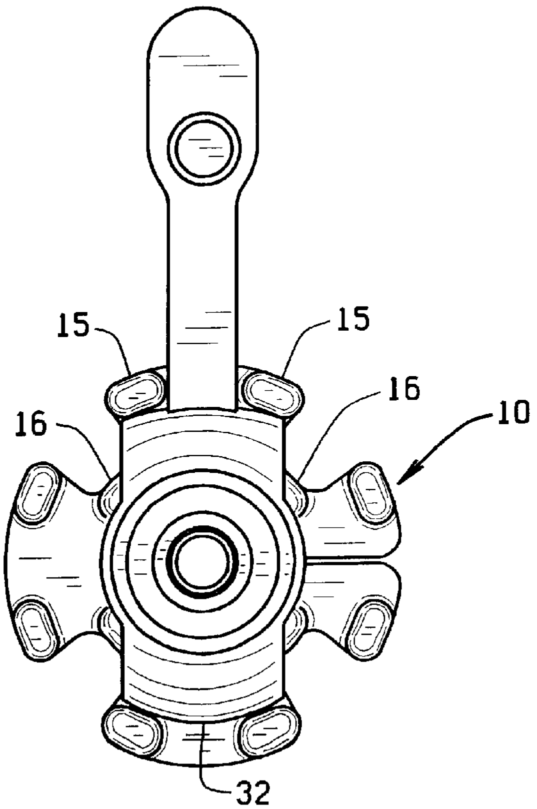
FIG. 4 is a planar view of the external retention member engaged to the shim device according to the present invention.

Referring to the drawings, the preferred embodiment of the shim device of the present invention is illustrated and generally indicated as 10 in FIG. 1*a*. The shim device 10 comprises a shim body 12 which forms four substantially identical outer portions 24 that surround an inner portion 26. Inner portion 26 forms an axial opening 22 through shim body 12 with a radial slit 20 that extends from opening 22 to an outer edge 40 through one of the outer portions 24. As shall be discussed in greater detail later, slit 20 is adapted to be spread apart by the user, as shown in FIGS. 1*b* and 4, so that the tubular member 36 of a low profile gastrostomy tube 11 may be slipped through slit 20 and engaged around axial opening 22. Preferably, slit 20 is located so that one of the outer portions 24 is split evenly in half as illustrated in FIG. 1*a*, although slit 20 may also be located along any portion of the shim body 12 and fall within the scope of the present invention.

Figure 2:
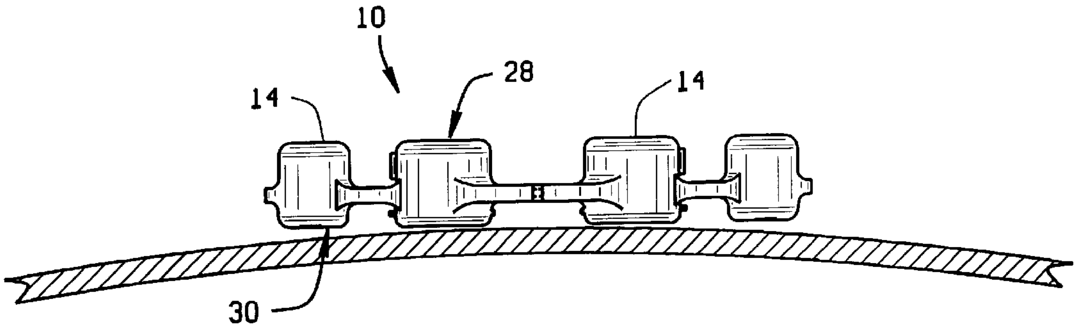
FIG. 2 is a side view of the shim device seated on a patient's body according to the present invention.

Two opposed apertures 18 are located on either side of axial opening 22 and are formed through shim body 12 for providing air flow circulation to the patient's outer skin layer when the low profile gastrostomy tube 11 is attached to a patient. Referring to FIG. 2, support pads 14 are provided to support and evenly distribute the weight of the external retention member 32 along the patient's outer skin layer as well as engage and orient the legs of the external retention member 32 properly when member 32 is seated on the shim device 10 (FIG. 4). Referring specifically to FIG. 1*a*, support pads 14 comprise a pair of outer pads 15 which are formed along the outer edge 40 of each outer portion 24, while a larger, inner pad 16 is in juxtaposition between each outer portion 24 around the inner portion 26.

As illustrated in FIG. 2, the shim body 12 includes opposing sides 28, 30 which are substantially identical with the exception of the height differential between the support pads 14 formed on each respective side 28, 30 of body 12. Preferably, support pads 14 on side 28 are all 2.5 mm tall, while those pads on side 30 are all 4.0 mm tall. The height differential between support pads 14 on each side 28, 30 permits one shim device 10 to accommodate both small and large sized external retention members 32 as required.

Figure 3A:
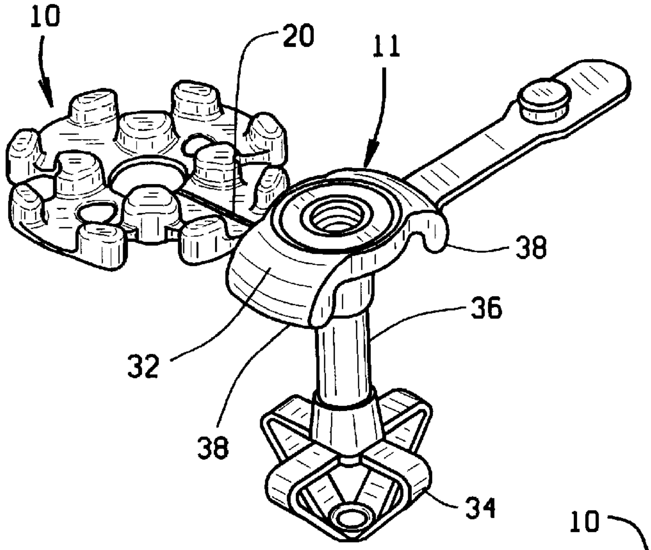
FIGS. 3*a–d* are isometric views of the engagement sequence showing the shim device being engaged to an external retention member according to the present invention.
Figure 3B:
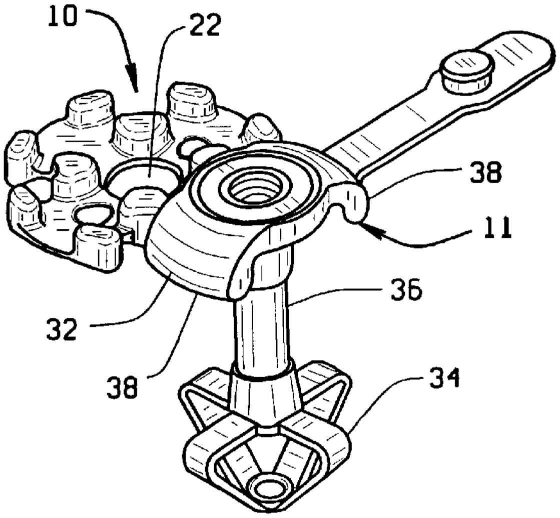
Figure 3C:
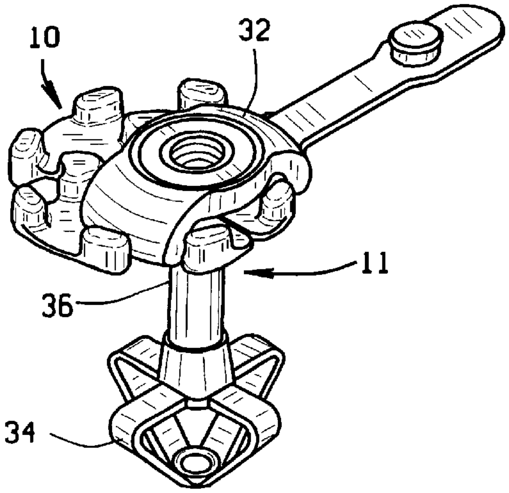
Figure 3D:
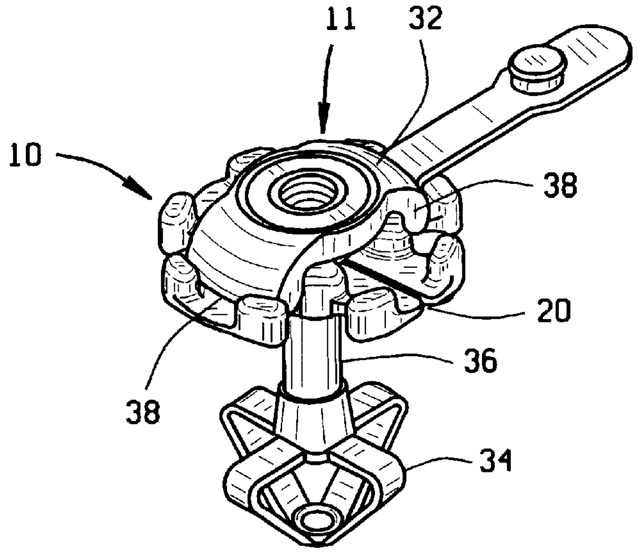

Referring to FIGS. 3*a–d*, the method for attaching the shim device 10 to the low profile gastrostomy tube 11 is disclosed without the patient shown for purposes of illustration. In FIG. 3*a*, the user orients the slit 20 of the shim device 10 toward the tubular member 36 of the low profile gastrostomy tube 11 and spreads apart slit 20. The user then lifts up on the legs 38 of the external retention member 32 with his fingers (not shown), and places the shim device 10 under the external retention member 32 as illustrated in FIG. 3*b*. This is done by allowing the tubular member 36 to pass through slit 20 as shown in FIG. 3*c* until member 36 is fully engaged around axial opening 22. Referring to FIG. 3*c*, the shim device 10 is shown fully engaged to the low profile gastrostomy tube 11 when the legs 38 of the external retention member 32 are fully positioned between the outer and inner pads 15, 16 of shim body 12. This orientation of legs 38 between support pads 14 is best shown in FIG. 4, whereby legs 38 are seated between the outer and inner pads 15, 16 so that the weight of external retention member 32 is supported by the shim body 10 and evenly distributed 12 along the patient's outer abdominal wall. The even weight distribution by shim device 10 is accomplished through the plurality of support pads 14 which are in contact with the patient's body, while pads 14 formed on the opposite side of shim body 12 engage and properly orient the external retention member 32 to the shim device 10.

It will be appreciated that when the shim device 10 according to the present invention is properly engaged to the low profile gastrostomy tube 11, the entire external retention member 32 is supported upon shim body 12 so that only support pads 14 contact the patient's body.

It will be further appreciated that the height differential between the two support pads 14 formed on opposite sides 28, 30 of shim body 12 permits the user to easily accommodate a range of spaces formed between a patient's abdominal wall and the underside of the external retention member 32 by merely flipping over the shim device 10.

It will even be further appreciated that the heights of support pads 14 on each side 28, 30 are not restricted to 2.5 mm and 4.0 mm, respectively, as disclosed on the preferred embodiment. In the alternative, support pads 14 on each side 28, 30 may be of any suitable height which adequately accommodates patients of different sizes and builds.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

I/we claim:

1. A shim device comprising:

a shim body having opposed sides, said shim body including an inner portion having an axial opening formed therethrough, said shim body further including at least one outer portion defining an outer edge radially extending outwardly from said inner portion, said at least one outer portion having a radial slit formed therethrough;

a first plurality of support pads formed on one of said opposed sides and extending a first height; and a second plurality of support pads formed on the other of said opposed sides and extending a second height therefrom, said first plurality of support pads formed on one of said opposed sides mirroring the second plurality of support pads on the other of said opposed sides, wherein either one of said first or second plurality of support pads provides a base and the other of said first or second plurality of support pads provides a support surface.

2. A shim device according to claim 1, wherein said at least one outer portion comprises four outer portions.

3. A shim device according to claim 1, wherein said first height is approximately about 2.5 millimeters, and wherein said second height is approximately about 4.0 millimeters.

4. A shim device according to claim 1, wherein said shim body further comprises at least one aperture.

5. A shim device according to claim 4, wherein said at least one aperture comprises two apertures oppositely disposed about said axial opening.

6. A shim device according to claim 1, wherein said radial slit extends between said axial opening and said outer edge.

7. A shim device according to claim 1, wherein said first plurality and said second plurality of support pads each include a plurality of outer pads proximate said outer edge, and wherein said first plurality and said second plurality of support pads each include a plurality of inner pads disposed on said inner portion proximate said axial opening.

8. A shim device according to claim 2, wherein said first plurality and said second plurality of support pads each include a plurality of outer pads proximate said outer edge, and wherein said first plurality and said second plurality of support pads each include a plurality of inner pads disposed proximate said axial opening.

9. A shim device according to claim 8, wherein said outer pads comprise two outer pads disposed on said at least one outer portion.

10. A shim device according to claim 8, wherein said inner pads comprise four pads disposed on said inner portion and aligned approximately between each of said four outer portions.

11. A shim device according to claim 1, wherein said shim device is constructed from a flexible, resilient material.

12. A method for attaching a shim device to a gastrostomy device, said gastrostomy tube comprising a retention member, said retention member including a plurality of legs that extend therefrom, said method comprising the steps of:

(a) providing a shim device comprising a shim body having opposed sides, said shim body including an inner portion having an axial opening formed therethrough, said shim body further including at least one outer portion defining an outer edge radially extending outwardly from said inner portion, said at least one outer portion having a radial slit formed therethrough, a first plurality of support pads formed on one of said opposed sides and extending a first height, a second plurality of support pads formed on the other of said opposed sides and extending a second height therefrom, said first plurality of support pads formed on one of said opposed sides mirroring the second plurality of support pads on the other of said opposed sides;

(b) determining which of said opposed sides is to engage said legs and which other of said opposed sides is to provide a base;

(c) orienting said shim device towards one of said opposed sides;

(d) spreading said slit such that said tubular member may be passed therethrough;

(e) lifting the legs of the retention member;

(f) passing said tubular member through said slit and into said axial opening; and (g) positioning the shim device such that the legs are seated between said outer legs and said inner pads.

13. A method for attaching a shim device to gastrostomy tube according to claim 12, wherein said step of lifting the legs of the retention member further comprises lifting the legs with the user's hand gripped between a user's thumb and forefinger.

* * * * *